United States Patent
Popescu et al.

(10) Patent No.: US 7,860,126 B2
(45) Date of Patent: Dec. 28, 2010

(54) METHOD AND DEVICE FOR DATA TRANSMISSION BETWEEN TWO COMPONENTS MOVING RELATIVE TO ONE ANOTHER

(75) Inventors: Stefan Popescu, Erlangen (DE); Dieter Cherek, Hirschaid (DE)

(73) Assignee: Siemens Aktiengesellschaft, Munich (DE)

( * ) Notice: Subject to any disclaimer, the term of this patent is extended or adjusted under 35 U.S.C. 154(b) by 51 days.

(21) Appl. No.: 11/996,394

(22) PCT Filed: Jul. 12, 2006

(86) PCT No.: PCT/EP2006/064150

§ 371 (c)(1), (2), (4) Date: Jan. 22, 2008

(87) PCT Pub. No.: WO2007/012568

PCT Pub. Date: Feb. 1, 2007

(65) Prior Publication Data

US 2008/0205446 A1    Aug. 28, 2008

(30) Foreign Application Priority Data

Jul. 27, 2005   (DE)   ........................ 10 2005 035 207

(51) Int. Cl.
H04J 3/24   (2006.01)

(52) U.S. Cl. ..................................... 370/473; 370/230

(58) Field of Classification Search ................. 370/473; 378/15, 4, 194, 110, 101–109, 10, 19
See application file for complete search history.

(56) References Cited

U.S. PATENT DOCUMENTS

| 4,181,850 | A |   | 1/1980  | Fairbairn |
|-----------|---|---|---------|-----------|
| 4,486,739 | A | * | 12/1984 | Franaszek et al. ............. 341/59 |
| 5,535,033 | A | * | 7/1996  | Guempelein et al. ........ 398/114 |
| 6,292,919 | B1 |  | 9/2001  | Fries et al. |
| 6,327,327 | B1 | * | 12/2001 | Herold et al. .................. 378/15 |
| 2003/0185338 | A1 | | 10/2003 | Dafni et al. |
| 2004/0141686 | A1 | | 7/2004  | Schilling et al. |

FOREIGN PATENT DOCUMENTS

WO    WO 03/053246    *   7/2003

* cited by examiner

Primary Examiner—Kwang B Yao
Assistant Examiner—Adam Duda
(74) Attorney, Agent, or Firm—Schiff Hardin LLP

(57) ABSTRACT

In a method and a device for data transmission between two components moving relative to each other, a first of the components has a number of transmission segments arranged along the movement direction and a second of the components has receiver units arranged along the movement direction. The data to be transmitted are divided among several transmitter segments for parallel transmission thereof. The data to be transmitted are configured in respective data packets, each having a packet identifier in addition to a data portion. A receiver device connected to the receiver units assembles the respective data portions of the respective received packets in a correct sequence using the respective packet IDs. The need for a position detector for noting the relative position of the transmitter segments and the receiver units is avoided.

15 Claims, 2 Drawing Sheets

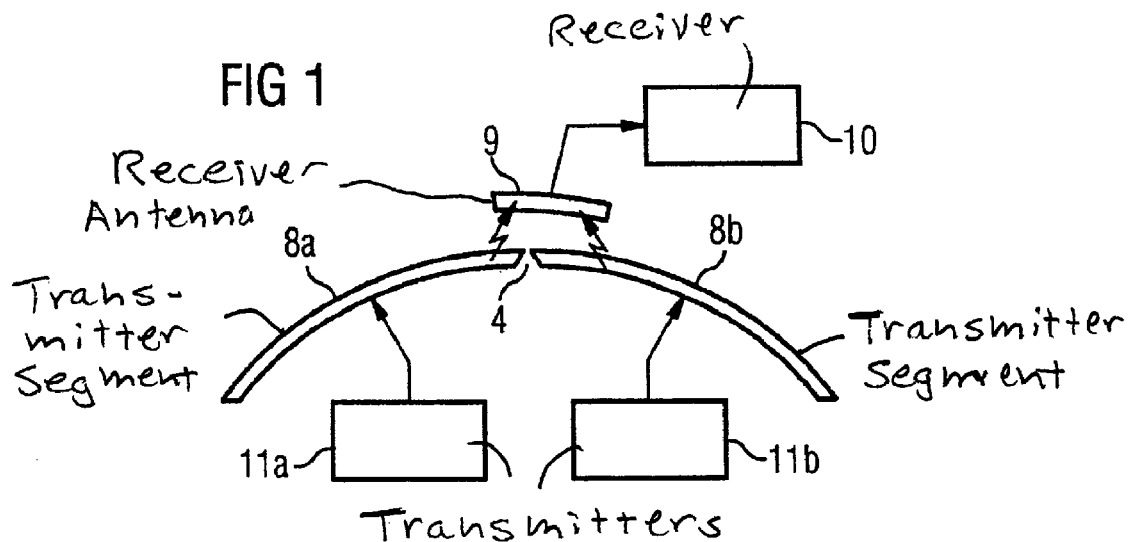
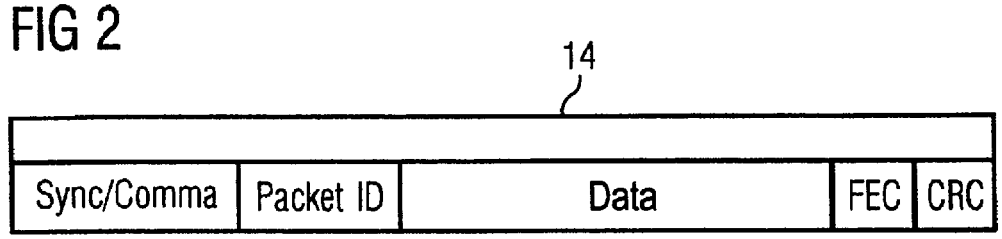
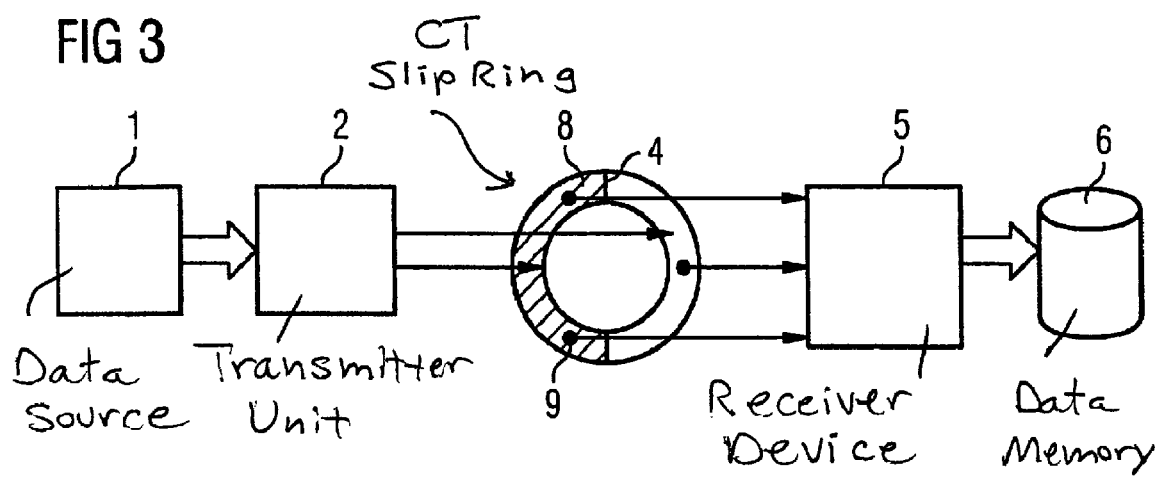

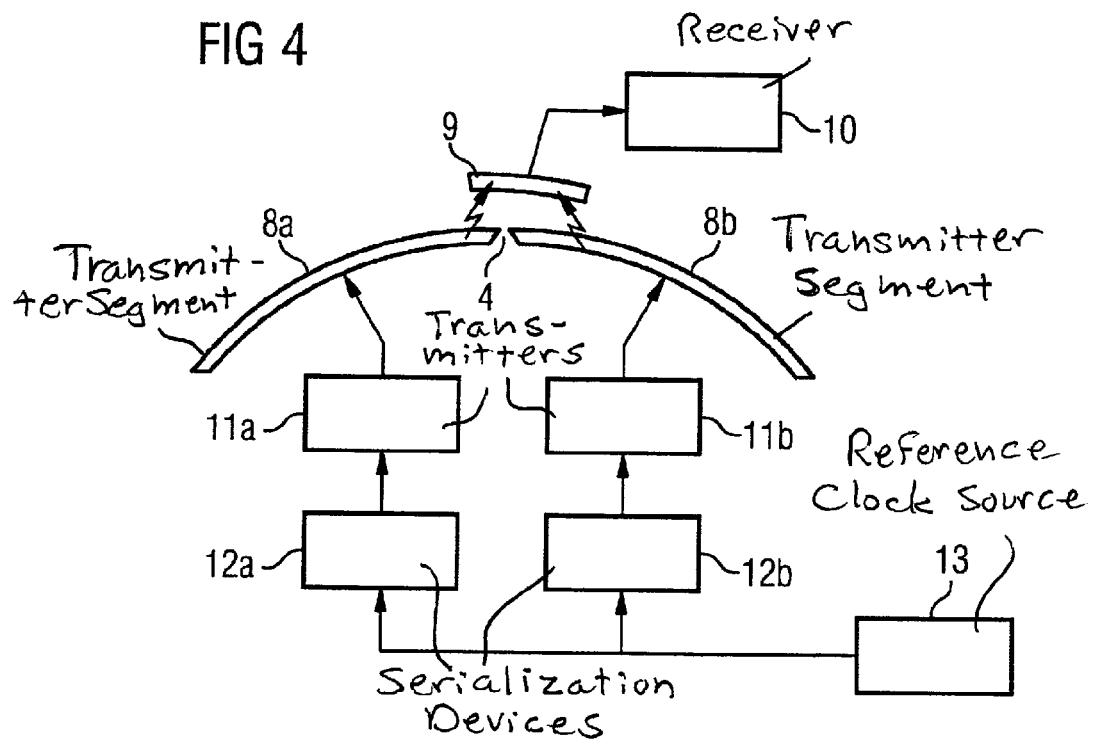
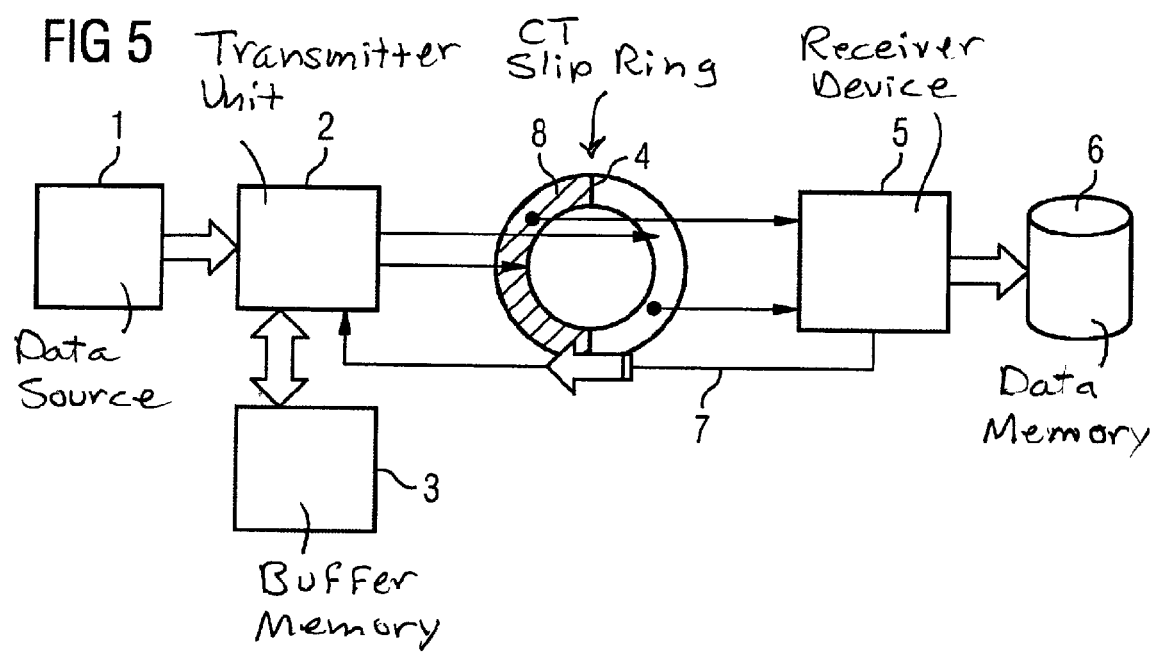

METHOD AND DEVICE FOR DATA TRANSMISSION BETWEEN TWO COMPONENTS MOVING RELATIVE TO ONE ANOTHER

BACKGROUND OF THE INVENTION

1. Field of the Invention

The present invention concerns a method and a device for data transmission between two components moving relative to one another, in particular between the rotating part and the stationary part of a computed tomography apparatus, of the type wherein the first component has a number of transmission segments arranged along a movement direction and the second component has a number of receiver units arranged along the movement direction, the spacing of which is less than or equal to a center distance of the transmission segments and wherein the data are divided for parallel transfer to a number of the transmission segments, and each receiver unit receives data only from the transmission unit in whose immediate proximity it is directly located.

2. Description of the Prior Art

In imaging medical technology (a primary application field of the present invention), computed tomography systems are frequently used in which a very large number of measurement data are acquired in a short time, and are transmitted to an image reconstruction unit and further processed therein to reconstruct the desired images. The data transmission system required for this purpose must enable a high speed transfer (due to the large number of measurement data accumulating per time unit) and must also ensure an optimally disruption-free transmission between the rotating part and the stationary part of the computed tomography system. The techniques of capacitive coupling as well as optical coupling that can also be used in the present method and the present device, are the primarily used techniques for the data transfer between the rotating part and the stationary part.

For example, U.S. Pat. No. 5,140,696 A describes a device for signal transmission between two components moving relative to one another, in particular in a computer tomograph in which a circular strip conductor is arranged as a transmitter at the periphery of the rotating part of the gantry and a short segment of a strip conductor is arranged as a receiver antenna at the stationary part of the gantry in immediate-proximity to the transmitter conductor. With this capacitive coupling technique the data are modulated on a carrier signal and injected into the circular strip conductor. A portion of the signal energy of the electromagnetic signal propagating in the strip conductor can be detected by the receiver antenna at the stationary part as a result of the radiated energy that is present in the intervening space between the two parts rotating counter to one another. After demodulation, the data are then available at the stationary part. However, with the increasing data rate of modern computed tomography systems (in particular multi-line systems) the transmission capacity of a single pair (composed of strip conductor and receiver antenna) is no longer sufficient, such that at least two such pairs must be arranged next to one another in order to be able to transfer the accumulating data in real time. This increases the costs of the transfer system, requires additional structural space at the rotating part and increases its weight.

To increase the transmission capacity, U.S. Pat. No. 6,327,327 teaches subdividing the circular rotary strip conductor into a number of segments that are separated from one another and to provide a corresponding number of receiver antennas at the side of the stationary part. The data to be transmitted can then be divided among the multiple transmission segments and can be transmitted in parallel between the transmitter segments and the receiver antennas. Each transmitter segment is thereby connected with its own transmitter that respectively transmits a subset of the accumulating data to the currently opposite receiver antenna. The transmission capacity of the data transmission system is increased by this provision of a number of parallel transmission channels. With this technique, however, transmission problems regularly occur when a receiver antenna moves directly over the gap between two adjacent transmission segments. In this time span the antenna receives data from two transmission segments since, for a sufficient reception quality, it cannot be executed arbitrarily short. Given an arrangement with N transmission segments this problem occurs N times during a complete rotation of the gantry. The respective time span of such an interruption depends primarily on the length of the receiver antenna as well as the rotation speed of the gantry. For low data rates of, for example, 60 Mbps the bit length in the micro-strip conductor is 333 cm and the required length of the receiver antenna is 25 cm in order to achieve a sufficient transmission quality. The large length of the receiver antenna is based on the decreasing coupling capacity for the low-frequency transmission components. At higher data rates the antenna can be executed shorter. Given a data rate of, for example, 2500 Mbps the bit length in the micro-strip conductor is 8 cm and the required length of the receiver antenna is 4.3 cm, such that shorter interruption time spans result. The amount of data that is lost in the interruption time spans also simultaneously increases given a higher data rate.

To solve this problem, in U.S. Pat. No. 6,327,327 it is proposed to use two parallel arrangements composed of an annular, segmented strip conductor and receiver antenna whose transmitter segments are offset counter to one another in the circumferential direction. The data reception is then respectively switched between the two arrangements when the receiver antennas are respectively directly located between two transmitter segments in an arrangement. The arrangement of two parallel arrangements again increases the costs, requires additional structural space at the rotating part and increases its weight.

Furthermore, for reconstruction of the data received via the receiver antennas as well as for switching between the arrangements, an angle transmitter is required in the arrangement of U.S. Pat. No. 6,327,327, from whose signals the current position of the transmission segments relative to the receiver antennas can be derived. This information required in the receiver device in order, among other things, to be able to assemble the segments of the serial bit stream received by the different receiver antennas in the correct order.

SUMMARY OF THE INVENTION

An object of the present invention is to provide a method and a device for data transmission between two components moving relative to one another, in particular between the rotating part and the stationary part of a computed tomography apparatus, wherein no knowledge of the current position of the transmitter segments relative to the receiver units is required for the data transmission.

In the inventive method for data transmission between two components moving relative to one another, the first of the two components having a number of transmitter segments separated from one another and arranged along a movement direction, and the second of the two components having a number of receiver units arranged along the movement direction, for example receiver antennas in the case of a capacitive coupling, the spacing of the receiver units is smaller than or equal to a center distance of the transmitter segments, so each of the receiver units receives data only from the transmitter segment in whose immediate proximity it is directly located. In the inventive method the data are divided in a known among a number of transmitter segments for parallel transfer. In accordance with the invention the data are transmitted in small data packets that, in addition to a data portion (known as the payload) each contain at least one packet ID (ID: identification character string) using which the data portions of the data packets are assembled in the correct order in a receiver device connected with the receiver units. The data packets also each advantageously contain an error check code, for example a CRC sum (CRC: cyclic redundancy check).

By the inventive transmission in small data packets with the packet ID (in the simplest case a consecutive number), given the use of the data transfer system in a computed tomography apparatus, an angle transmitter can be foregone. The receiver device with the receivers that are connected with the individual receiver units can assemble the data transferred with the data packets in the correct order solely on the basis of the packet ID unique to the transfer. Given use of an error check code, incorrect data packets (which normally originate from receiver units that were located directly over the gap between two transmitter segments during the reception) can additionally be detected in the receiver device.

In the present method and the associated device the data are thus assembled into small data packets (which are identifiable via a unique packet number (packet ID)) in the transmitter device, which comprises a data multiplexer, a data packet generator and a plurality of transmitters. These data packets are supplied via the transmitter segments connected with the transmitters and the receiver units with the associated receivers to a demultiplexer in the receiver device The demultiplexer uses the packet ID in order to recognize the origin of each data packet and to arrange the data packets (or, respectively, their data content) that are received by different receivers in the correct order. In this manner no further information about a relative position between moving components is required.

In a preferred embodiment, transmission errors can be detected via the error check code (for example a CRC code) simultaneously transmitted in each data packet. The data packet generator calculates the error check code on the basis of the data portion (payload) of the respective data packet and a specific generation polynomial or algorithm and attaches it to each data packet. In the receiver device the error check code is calculated on the basis of the same method and is compared with the error check code contained in the data packet. In this manner incorrect data packets can be detected, which incorrect data packets can, for example, occur in the interruption time spans described above in which a receiver unit is located directly between two transmitter segments.

The problem of the interruption time spans discussed above can be circumvented with different techniques in the present method and the associated device, such as following preferred embodiments.

In a first embodiment of the method and the associated device, a redundant number of receiver units is used. The number of the receiver units is thereby selected higher than the number of the transmitter units, such that the spacing of the receiver units is smaller than the center distance of the transmitter segments. This results in, at any point in time at which a receiver unit is located directly between two transmitter segments, a further receiver unit being respectively moved directly over the two transmitter segments and thus the data from the two transmitter segments are received without error via these two further receiver units. At the receiver device, the incorrect data packet can then be detected and discarded based on the error check code, so no interruption of the data transfer occurs due to the error-free data packets from the two further receiver units.

In a further embodiment of the method and the associated device, the problem of the interruption time spans is solved in a different manner, wherein a redundant number of receiver units and receivers is not required. In this embodiment an elastic buffer memory is used that for a period of time caches at least the set of data packets or data that have been transmitted in an interruption time span or that could have been lost in the transmission. This cache is advantageously dimensioned such that it has sufficient capacity in order to be able to accept both the cached data packets or data and the newly received data for the transmission during the transmission time span following an interruption time span. In the case of the data transmission in a computed tomography apparatus, the size of the buffer memory is selected dependent on the smallest rotation speed and the gap width between the transmitter segments, such that overall no data loss occurs. For an error-free data transmission, in this embodiment a receiver signal (acknowledgement signal) relating to the received data packet is then sent to the transmitter device when the data packet has been received without error. The error-free transmission can be established using the error check code. Upon establishment of an error no receiver acknowledgement signal is sent, such that given the absence of the acknowledgement signal the transmitter device carries out the transmission of this data packet again until a corresponding signal is received. The re-transmission of the data packet is enabled via the buffer memory. In the same manner it is naturally also possible to send an explicit error signal in the event that an incorrect data packet is detected. Furthermore, the possibility exists to send a single acknowledgement signal for a group of data packets that have been received within a predetermined transmission time span via a single channel or via multiple, but less than all of the channels, or via all parallel channels. For example, in the case in which all receiver units and gaps are synchronized so that the interruption time spans occur simultaneously for all channels, a single acknowledgement signal can be used as a gating signal that forces the repeated re-transmission until the interruption time span ends. The absence of a data packet can also be detected using the packet ID of the received data packets. The data portions of an absent data packet or an incorrect data packet also can be, under appropriate circumstances, interpolated from the adjacent data packets via suitable techniques, such that then no re-transmission must ensue.

The technique just described requires the availability of at least one 1-bit return channel between the receiver device and the transmitter device. Such a return channel is already present in computed tomography systems that use capacitive coupling for data transmission. The re-transmission of data packets (described above) on the basis of the return connection can naturally be used for errors arising due to any cause in data packets, or given missing data packets, such that any type of transmission errors during the entire data transmission can be corrected.

In a further embodiment of the present method and the associated device that can also be combined with the preceding or subsequently explained embodiments, an error correction code, in particular an FEC code: (FEC: forward error correction), is additionally transmitted with each data packet. Individual errors in the data packet can be automatically corrected by the receiver device on the basis of this additional information in each data packet. This also reduces the effective interruption time spans.

In an embodiment of the present method as well as of the associated device that can be combined with the preceding embodiments, all transmitters of the transmitter device obtain their clock signal from a common reference clock source with which they are connected. This makes the re-acquisition of the bit-clock in the serial bit stream by the receiver easier. A control bit sequence (known as a sync symbol or comma) is advantageously additionally transmitted in the data packets, on the basis of which control bit sequence the byte synchronization ensues in the receivers. The receivers must identify the correct byte limits in the reacquired serial bit stream. Via the common reference clock source of the transmitter and the transmission of the sync or comma symbol in the data packets, the receivers can more quickly synchronize to the transmitters changing with the movement. This in turn reduces the interruption time span upon changing between different transmitter segments. Furthermore, the transmission signal is advantageously centrally injected into the respective transmission segments, such that it propagates in opposite directions to both ends of the respective transmission segment with the same speed. When the length of all transmission segments and connection cables to these segments is selected the same for all transmitters, the phase of the bit clock is then approximately the same at the adjoining ends of adjacent transmitter segments. This results in a faster phase re-synchronization in the PLL of the receiver when this passes the gap between the transmitter segments and therewith additionally reduces the re-synchronization time after a change between two transmitter segments.

The present invention is naturally not limited to the use of capacitive coupling between the transmitter segments and receiver units (which, in this case, are fashioned as receiver antennas or short micro-strip conductors). For example, an optical coupling technique can also be used in which the transmitter segments are formed as a strip conductor composed of a dielectric layer with electro-optical properties between two strips made from an electrically-conductive material. The receiver unit in this case has at least one light source and an opto-electronic detector. During the movement of the receiver unit along a transmitter segment, a light beam of the light source is directed onto the dielectric layer of the strip conductor and reflected or transmitted with the opto-electronic detector, or diffracted beam portions are detected. A local temporal change of optical properties of the dielectric layer that is caused by the transmitter signal propagating therein can then be derived from the detected temporal intensity curve and the transmitter signal can be reconstructed. A further example for an optical coupling technique is found in U.S. Pat. No. 5,535,033.

Although the primary application field of the present method and the associated device concerns the data transmission between the rotating part and the stationary part of a computed tomography system, the method and the device can also be used for other applications in which two components move relative to one another at a slight distance and the data transmission simultaneously ensues via a number of transmission channels formed by corresponding transmitter segments and receiver units. This also applies for straight-line movements or other movements in which the transmitter segments move over the receiver units or vice versa at least during a segment of the movement.

BRIEF DESCRIPTION OF THE DRAWINGS

FIG. 1 schematically illustrates a section from a segmented, annular strip conductor that is moved in close proximity passed a receiver antenna.

FIG. 2 schematically illustrates an embodiment for the structure of a data packet in accordance with the present invention.

FIG. 3 schematically illustrates an embodiment of a data transmission device constructed and operating in accordance with the present invention.

FIG. 4 schematically illustrates a further embodiment of a sect ion through a segmented, annular strip conductor that moves past a receiver antenna.

FIG. 5 schematically illustrates a further embodiment of a device according to the present invention.

DESCRIPTION OF THE PREFERRED EMBODIMENTS

The above-discussed problem in the data transmission using separated transmitter segments 8a, 8b is illustrated in FIG. 1. FIG. 1 schematically shows a section from a segmented, annular strip conductor (also called a slip ring in the following), of which two of the transmitter segments can be seen, between which a gap 4 exists. The signals fed into the transmitter segments 8a, 8b via the transmitters 11a, 11b are received by the receiver antenna 9 past which the transmitter segments 8a, 8b move at a slight distance. The data to be transferred are thereby divided among the different transmitters 11a, 11b and transmitter segments 8a, 8b in order to form to transmission channels via which different data can be simultaneously transferred. As long as the receiver antenna 9 connected with the receiver 10 is located only over one of the transmitter segments, an error-free data transmission can ensue. In the time segment in which the receiver antenna 9 is, however, located over the gap 4, data are received from both transmitter segments. Due to the mixing between the different data, this leads to an incorrect data transmission in this time span, which should be avoided according to the embodiment of the present method and the associated device.

In the present method the data transmission ensues in small data packets that comprise at least one data part as well as a packet ID. FIG. 2 shows an example for such a data packet 14 as it is fashioned in an advantageous embodiment of the method as well as of the associated device. This data packet 14 includes a sync symbol at the start of the do that can be transmitted, for example, by means of an 8B/10B code between the transmitters and receivers. This serial coding technique provides an embedded clock signal and enables the integration of special sync and control sequences. The data transmission ensues serially, such that the bytes or words that represent the transferred data (in particular measurement data) are transferred in a serial bit stream. A clock re-acquisition device that re-acquires the clock frequency from the transmitted bit stream on the basis of a PLL (and therewith can read out the transmitted data) is provided in the respective receiver. Due the constant change of the data reception between the individual transmitter segments, the receiver must be in the position to re-acquire the phase and frequency synchronization as quickly as possible after the switching from one transmitter segment to another. The same applies for the byte synchronization on the basis of which the receiver can detect the correct byte limits. This byte synchronization ensues on the basis of the sync symbol embedded in the data packet.

In the present method and the associated device, each data packet carries a unique packet number (the packet ID) using which the data packets received in the receiver device or their transmitted data can be reassembled in the correct order. The packet ID must thereby be unique for each data packet during a transmission. This packet ID is generated in a packet generator in the transmitter device.

In the present example the data payload (i.e. the data transmitted in this packet) follows after the packet ID. A corrector code (an FEC) using which a limited number of transmission errors can be corrected is embedded following this data payload. The FEC block is calculated by the transmitter device and attached to each data packet. According to a known procedure, the information in the FEC block can then be used in the receiver device in order to correct some transmission errors. By a check of the CRC code further contained in the data packet it can subsequently be established whether additional errors are present. By the use of the FEC block the interruption period can be additionally reduced since, due to the correction possibility, the data transmission still functions given a smaller number of errors. Furthermore, the FEC block can be used in order to also correct errors occurring during the interruption-free transmission phases.

FIG. 3 shows an example for the schematic design of the present device as it can, for example, be used in a computed tomography apparatus. In this example the slip ring at the rotating part of the computer tomograph is constructed from only two transmitter segments 8 that are separated from one another by a gap 4. Naturally, the number of the annularly arranged transmitter segments can also be selected distinctly larger. In the example of FIG. 3 a redundant number of receiver antennas 9 is selected, such that the spacing of the receiver antennas 9 is smaller than the center distance of the two transmitter segments 8. In the present method and the present device the transmitter segments 8 are normally of the same length and have the same spacing. The same applies for the receiver antennas 9.

The measurement data are transmitted from the data source 1 (for example the detector unit of a computer tomograph) to the transmitter unit 2 which comprises at least one data multiplexer and a packet generator. In this transmitter device 2 the data are transmitted to two transmitters (not shown) that feed the two transmitter segments 8 with the data signals to be transmitted. Each of the two transmitter segments 8 thereby receives a different part of the data, wherein the transmission of these data ensues simultaneously in the data packets shown in FIG. 2. The data fed into the transmitter segments 8 are received by the receiver antennas 9 which are located in the immediate proximity of the respective transmitter segments 8 and are relayed to the receivers 10 and further into the receiver device 5. The transmitter segments 8 hereby rotate with the rotating part of the gantry while the receiver antennas 9 are attached to the stationary part. The transmitter segments 8 thus move past the receiver antennas 9. In the receiver device 5 (which comprises at least one data demultiplexer) the data packets are assembled in the correct order corresponding to their packet ID and the data are extracted from the data packets. The data are finally stored in a data memory 6 for further processing, in particular for image reconstruction.

In the present example three receiver antennas 9 with associated receivers are provided for the two transmitter segments 8. It is thereby achieved that, even when one of the receivers is located over the gap 4, the two other receivers can receive the data from the two transmitter segments 8 without error. In the receiver device 4, which data packet is incorrect (i.e. originates from the receiver located directly over the gap 4) is thus established using the CRC code so that this data packet can be discarded. However, since the two remaining receiver antennas 9 are not located over a gap but rather are respectively located directly above one of the two transmitter segments 8, all data or, respectively, data packets are nevertheless received without error and without data loss.

FIG. 4 schematically shows in section two transmitter segments 8a, 8b with an associated receiver antenna 9 with receiver 10 that is located over the gap 4 between the two transmitter segments 8a, 8b. The two transmitter segments are operated by two separate transmitters 11a, 11b that are in turn connected with separate serialization devices 12a, 12b. Both transmitter devices 11a, 12a or, respectively, 11b, 12b receive their clock signal from a common reference clock source 13. Furthermore, the transmitter signals are fed centrally into the respective transmitter segments 8a, 8b. This leads to the situation that, upon the receiver antenna 9 sweeping over the gap 4, the receiver 10 requires a shorter time for the re-synchronization since the frequency and the phase shift between the two adjoining ends of the transmitter segments 8a, 8b is only minimal. The frequency and phase synchronization can thus ensue very quickly, such that the interruption time is less overall.

FIG. 5 shows a further example for a device according to the present invention that manages without a redundant number of receiver antennas 9 and associated receivers. In this example an elastic buffer memory 3 is provided on the one hand that caches the transferred data for a sufficient time span. In the receiver device 5 the data packets received from the receiver antennas 9 are checked for defectiveness. If no errors are determined, an acknowledgement signal is transmitted to the transmitter device 2 via a return channel 7. In the case of a detected error or a data packet that is not received, no acknowledgement signal is sent. In this case the transmitter device 5 transmits the corresponding data packet again via retrieval from the buffer memory 3. This is repeated until an acknowledgement signal is received. Given a number of successive incorrect or not-received data packets, the retransmission naturally ensues in the same manner.

In a further preferred embodiment of the present device, for the use in a computed tomography it is ensured that the data transmission also functions in what is known as an overview or topogram mode. In this overview or topogram mode (a special scan mode in computed tomography) an exposure is generated either in lateral or antero-posterior view without rotation of the gantry. For this configuration the transmitter segments must be arranged displaced in terms of angle relative to the receiver units such that the receiver units are not located over a gap.

Although modifications and changes may be suggested by those skilled in the art, it is the intention of the inventors to embody within the patent warranted heron all changes and modifications as reasonably and properly come within the scope of their contribution to the art.

We claim as our invention:

1. A method for data transmission between first and second components that move relative to one another in a movement direction and at a movement speed, said first component comprising a plurality of transmitter segments arranged along said movement direction, each of said transmitter segments having a center distance from an edge thereof to a center thereof, and said second component comprising a plurality of receiver units spaced along said movement direction, with adjacent receiver units, among said plurality of receiver units, having a spacing therebetween that is less than or equal to said center distance, said method comprising the steps of:

organizing said data into data packets, and forming each data packet to include an error code, a data portion, and at least one packet identifier;

dividing said plurality of transmitter segments into a plurality of transmitter segment groups, with each of said transmitter segment groups comprising multiple adjacent transmitter segments in said plurality of transmitter segments;

from each of said transmitter segment groups, transmitting a plurality of said data packets in parallel from the multiple transmitter segments therein, to said receiver units, with each receiver unit receiving said data packet only from a transmitter segment in said group of transmitter segments that is located in immediate proximity to the receiver unit;

after transmitting said data packets from said group of transmitter segments, as transmitted data packets, storing the transmitted data packets for a predetermined time period in a buffer memory associated with said first component;

at said second component, after receipt of said transmitted data packets, using said error check code in each of the transmitted data packets to identify any non-error-free transmitted data packets, and transmitting a signal on a one-bit return line back to said first component that identifies said non-error-free transmitted data packets;

in one of said transmitter segments, receiving said signal from said one-bit return line and retrieving, as retrieved data segments, any of the transmitted data packets stored in the buffer memory that are identified in said signal, and re-transmitting said retrieved data packets to said second component; and at said second component, supplying the transmitted data packets received by said receiver units, that are not identified as non-error-free packets, together with the retrieved data packets that were re-transmitted, to a receiver device, as correctly-received data packets, and, in said receiver device, assembling the correctly-received data packets in a correct order using the respective packet identifiers of the correctly-received data packets.

2. A method as claimed in claim 1 wherein said receiver units have a spacing therebetween that is less than said center distance of said transmitter segments and comprising the additional step of, in said receiver device, using said error check code, selecting one error-free data packet from among all received data packets respectively having identical packet identifiers and using the data portion of said one error-free packet when assembling the received data packets in said correct order.

3. A method as claimed in claim 1 comprising supplying the respective transmitter segments with respective identical clock signals from a common reference clock source at said first component.

4. A method as claimed in claim 1 comprising centrally injecting the respective data packets into the respective transmitter segments from a transmitter device at said first component.

5. A method as claimed in claim 1 comprising transmitting said data packets between said transmitter segments and said receiver units by capacitive coupling.

6. A method as claimed in claim 1 comprising transmitting said data packets between said transmitter segments and said receiver units by optical coupling.

7. A method as claimed in claim 1 comprising additionally including, in each data packet, a sync symbol for byte synchronization in said receiver device.

8. A device for data transmission comprising:

first and second components moving relative to one another in a movement direction and at a movement speed, said first component comprising a plurality of transmitter segments arranged along said movement direction, each of said transmitter segments having a center distance from an edge thereof to a center thereof, and said second component comprising a plurality of receiver units spaced along said movement direction, with adjacent receiver units, among said plurality of receiver units, having a spacing therebetween that is less than or equal to said center distance;

a processor configured to organize said data into data packets, by forming each data packet to include an error code, a data portion, and at least one packet identifier;

said plurality of transmitter segments being divided into a plurality of transmitter segment groups, with each of said transmitter segment groups comprising multiple adjacent transmitter segments in said plurality of transmitter segments;

each of said transmitter segment groups transmitting a plurality of said data packets in parallel from the multiple transmitter segments therein, to said receiver units, with each receiver unit receiving said data packet only from a transmitter segment in said group of transmitter segments that is located in immediate proximity to the receiver unit;

said processor being configured after said data packets are transmitted from said group of transmitter segments, as transmitted data packets, to store the transmitted data packets for a predetermined time period in a buffer memory associated with said first component;

a processor at said second component configured to, after receipt of said transmitted data packets, use said error check code in each of the transmitted data packets to identify any non-error-free transmitted data packets, and to transmit a signal on a one-bit return line back to said processor at said first component that identifies said non-error-free transmitted data packets;

said processor at said first component being configured to receive said signal from said one-bit return line and retrieve, as retrieved data segments, any of the transmitted data packets stored in the buffer memory that are identified in said signal, and to re-transmit said retrieved data packets to said second component via one of said transmitter segments; and said processor at said second component being supplied with the transmitted data packets received by said receiver units, that are not identified as non-error-free packets, together with the retrieved data packets that were re-transmitted, as correctly-received data packets, and being configured to assemble the correctly-received data packets in a correct order using the respective packet identifiers of the correctly-received data packets.

9. A device as claimed in claim 8 comprising a common reference clock source at said first component that supplies the respective transmitter segments with respective identical clock signals.

10. A device as claimed in claim 8 wherein said transmitter device centrally injects the respective data packets into the respective transmitter segments at said first component.

11. A device as claimed in claim 8 wherein said transmitter segments and said receiver units interact by capacitive coupling to transmit said data packets.

12. A device as claimed in claim 8 wherein said transmitter segments and said receiver units interact by optical coupling to transmit said data packets.

13. A device as claimed in claim 8 wherein said transmitter device additionally includes, in each data packet, a sync symbol for byte synchronization in said receiver device.

14. A device as claimed in claim 8 wherein said first component is a component of a rotating part of a computed tomography apparatus and said second component is a component of a stationary part of said computed tomography apparatus.

15. A device as claimed in claim 14 wherein said receiver units at said stationary part are distributed along an annular carrier.

* * * * *